United States Patent [19]
Stewart

[11] Patent Number: 5,292,888
[45] Date of Patent: Mar. 8, 1994

[54] HIGH MELTING POINT STILBAZOLIUM SALTS

[75] Inventor: Kevin R. Stewart, Schenectady, N.Y.

[73] Assignee: General Electric Company, Schenectady, N.Y.

[21] Appl. No.: 82,704

[22] Filed: Jun. 28, 1993

[51] Int. Cl.⁵ .......................................... C07D 211/70
[52] U.S. Cl. ................................................ 546/347
[58] Field of Search ......................................... 546/347

[56] References Cited

U.S. PATENT DOCUMENTS 5,094,553  3/1992  Yakymyshyn et al. .............. 385/122
5,194,984  3/1993  Boden et al. ........................ 359/321

OTHER PUBLICATIONS

Marder et al., Science, vol. 246, "Synthesis of Organic Salts with Large Second-Order Optical Nonlinearities", pp. 626–628, Aug. 1989.

*Primary Examiner*—C. Warren Ivy
*Assistant Examiner*—Zinna N. Davis
*Attorney, Agent, or Firm*—William H. Pittman

[57] ABSTRACT

Stilbazolium salts that retain high second harmonic generation properties as well as high melting points are disclosed herein. More particularly, novel 4'-dimethylamino-N-methylstilbazolium cyclopentanesulfonate and homologs thereof which are expected to be useful in optoelectric devices and systems are disclosed.

3 Claims, No Drawings

HIGH MELTING POINT STILBAZOLIUM SALTS

The following invention was made with government support via contact number F49620-91-C-0075 which was awarded by the United States Air Force. The government has certain rights in this invention.

FIELD OF THE INVENTION

This invention relates to new compositions of matter and more particularly to stilbazolium salts that unexpectedly retain high second harmonic generation properties (nonlinear optical activity) as well as high melting points.

BACKGROUND OF THE INVENTION

The optics and electronics industries rely upon inorganic compounds for fabrication of various components. However, these industries may benefit largely from the plethora of organic compounds, both known and unknown. Of the many potential applications of organic compounds to the above-mentioned industries, many relate to the electro-optic effect as described by Kerr (1875) and Pockels (1906). Additionally, frequency doubling by second harmonic generation (SHG) is often considered. SHG may be defined as the doubling of light's fundamental frequency.

A test to study SHG has been developed (Kurtz and Perry, 1968) which analyzes, for instance, the noncentrosymmetric crystal structure of organic compounds. Organic compounds which posses a noncentrosymmetric structure exhibit optical nonlinearity and are generally said to be nonlinear.

Organic nonlinear optical materials displaying high SHG properties are potentially useful in applications which require high speed optical modulators. Such applications include high speed long distance data links and electric field sensors for use in electromagnetically noisy environments. In addition, such materials provide efficient wavelength shifting capability for optical and infrared remote sensing (e.g., of pollutant particulate concentration) and diode laser frequency doubling for optical data storage.

It has been of increasing interest to prepare organic nonlinear optical materials, such as stilbazolium salts, that posses high melting points without adversely affecting their SHG properties. High melting point stilbazolium salts are desirable because many processing steps involving such materials are conducted at temperatures that are near or greater than their conventional melting points. This often causes molecular breakdown or molecular restructuring of the materials which inevitably results in loss of nonlinear optical properties.

Description of the Prior Art

Accordingly, attempts have been made to prepare stilbazolium salts with high melting points. In commonly assigned U.S. Pat. No. 5,094,553, 4'-dimethylamino-4-methylstilbazolium p-toluenesulfonate (DAST) is disclosed. Said DAST has a favorable melting point range. However, as a result of its toluenesulfonate anion, the molecular dipoles within the crystals of the compound form a herringbone arrangement which characteristically reduces their SHG properties.

Other investigators have focused their attention on stilbazolium salts that posses favorable SHG properties. In commonly assigned U.S. Pat. No. 5,194,984, 4'-dimethylamino-4-methylstilbazolium methanesulfonate (DASMS) is disclosed. Crystals of said DASMS possess favorable SHG properties. However, since DASMS crystals contain a tetrahydrated methanesulfonate anion, they melt at lower temperatures and are more difficult to process.

Efforts to produce stilbazolium salts that unexpectedly retain high SHG properties and high melting points have not been disclosed.

The instant invention, therefore, is patentably distinguishable from the above-mentioned patents, since among other reasons, it is based on the discovery of stilbazolium salts that unexpectedly display high second harmonic generation properties as well as high melting points.

SUMMARY OF THE INVENTION

The instant invention is based on the discovery of stilbazolium salts that unexpectedly retain high second harmonic generation properties as well as high melting points. Said stilbazolium salts are represented by the formula

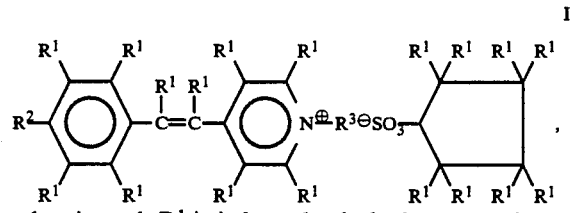

wherein each $R^1$ is independently hydrogen or deuterium, $R^2$ is HO—, $H_3CO$— or $(R^3)_2N$—. Each $R^3$ is independently an aliphatic, alicyclic or aromatic radical; however, methyl groups in which from 0 to 3 of the hydrogens are replaced by deuterium are preferred.

It is preferred that the stilbazolium salt of the instant invention is 4'-dimethylamino-N-methylstilbazolium cyclopentanesulfonate (DASCp) and represented by the formula

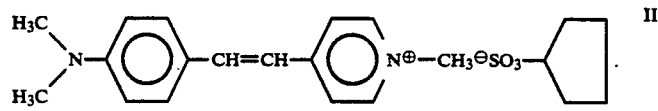

The present invention, therefore, is based on the discovery of stilbazolium salts that display high SHG properties as well as high melting points. High SHG properties may be defined as a second harmonic generation powder efficiency of at least about 1000 as compared to a urea standard which is assigned a value of 1 (SHG powder efficiency as described by Marder et al., Science, 245, 626–628 (1989). High melting points may be defined as at least about 230° C.

p The structures depicted hereinabove are not limited to any sterioisomeric (cis or trans) arrangement. However, the trans-isomer is often preferred in nonlinear optical applications. The cis- and trans-isomers may be separated by conventional methods such as fractional crystallization or flash column chromatography.

The additional features and advantages of the invention will be made evident upon reference to the following detailed description.

DETAILED DESCRIPTION OF THE PREFERRED EMBODIMENT

Materials that display high SHG properties have been prepared. The SHG properties of these materials are obtained in part by synthesizing and incorporating therein a salt in which the cation portion exhibits large molecular hyperpolarizability. Coupling said cation portion with a specific counterion (anion) can lead to materials that demonstrate favorable SHG properties.

No efforts, however, have been disclosed which address stilbazolium salts that retain high second harmonic generation properties as well as high melting points. In the case of DASMS (described above), its methanesulfonate anion exists as a tetrahydrate. Said anion is pentagonal and can be represented by the formula

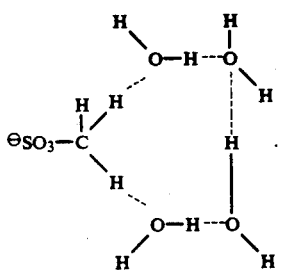

III

Because of this anion, the molecular dipole in DASMS crystals fully align along a common axis which results in a maximum bulk crystalline dipole. This maximum bulk crystalline dipole plays a critical role in giving DASMS its favorable SHG properties.

Nonetheless, the DASMS anion comprises hydrogen bonds which are susceptible to heat since their bond energies are on the order of only about 1.5 kcal/mol. As a result, DASM melts at temperatures that are lower than conventional processing (e.g., metal deposition) temperatures.

Conversely, DAST (described above) possesses a toluenesulfonate anion. Said toluenesulfonate anion comprises C—C and C—H covalent bonds which have bond energies on the order of about 100 kcal/mol. As a result, DAST has a melting point range on the order of about 40° C. greater than that of DASMS. Hence, it is readily processed.

Notwithstanding this fact, the SHG properties of DAST are approximately 20% less efficient than those of DASMS. This is true because DAST crystals do not fully align along a common axis as in the case of DASMS. In fact, the molecular dipoles within the crystals of DAST form a herringbone arrangement which leads to the above-mentioned decrease in SHG efficiency.

The instant invention therefore is based on the discovery of DASCp and homologs thereof. Said DASCp and its homologs contain anions as depicted by formulae I and II.

As a result of said anions (which are pentagonal as in the case of DASMS), the molecular dipole of novel DASCp crystals (or crystals of DASCp homologs) fully align along a common axis yielding SHG properties which are expected to be at least about 1000 as compared to a urea standard which is assigned a value of 1. Moreover, since said ions consist of carbon to carbon and/or carbon to hydrogen and/or carbon to deuterium covalent bonds, the melting points of DASCp and homologs thereof are high.

The stilbazolium salts described in the instant invention are expected to be useful in the fabrication of optical materials. Any light transmitting properties that may arise from said compounds are expected to be based on the different crystalline structures and degrees of hydration they may obtain. Moreover, it is expected that electro-optic modulators may be prepared from the compounds produced via the instant invention since they possess light transmitting properties which can possibly be varied by application of an electric field.

Additionally, it is anticipated that optical waveguides, such as those described in U.S. Pat. Nos. 5,094,553 and 5,194,984, may be prepared from the salts prepared via the instant invention since they may possess light transmitting properties resulting from predictable crystalline structures.

The stilbazolium salts of the instant invention may be prepared, for instance, by synthesizing cyclopentane sulfonic acid via the oxidation of cyclopentyl mercaptan with peroxy acetic acid. The sulfonic acid may subsequently be treated with silver oxide in order to produce a silver salt of the acid. Said salt may then be treated with a solution of methanol and dimethylamino N-methylstilbazolium iodide to produce dimethylamino stilbazolium cyclopentane sulfonate and a silver iodide precipitate. The precipitate can be recovered by conventional filtration methods and solid 4'-dimethylamino N-methylstilbazolium cyclopentane sulfonate may be obtained after methanol removal.

It should be noted that all reactants described herein may be deuterated or perdeuterated in order to produce a deuterium containing stilbazolium salt.

The following examples and table are provided to further facilitate the understanding of the invention, and they are not intended to limit the instant invention.

Moreover, all stilbazolium salts produced can be confirmed by conventional techniques such as proton and carbon 13 nuclear magnetic resonance spectroscopy as well as x-ray crystallographic techniques.

EXAMPLE 1

A one liter three-neck flask was charged with 300 mL of methylene chloride and 25 grams (245 mmole) of cyclopentyl mercaptan to produce a reaction solution. The reaction solution was chilled to 15° C. in an ice-water bath and followed by the addition of 190 mL of 35% peroxy acetic acid. Said peroxy acetic acid was added over a period of about 3 hours and the reaction solution was maintained at a temperature of about 18°–26° C. After the reaction solution was stirred overnight at room temperature, 100 mL of water and 25 grams of sodium bisulfite were added followed by 2 additional hours of stirring. The reaction solution was then reduced on a rotovap and the pH was adjusted with dilute hydrochloric acid until a white solid precipitate formed. Said precipitate was isolated via filtration and dried in vacuo (50% yield of cyclopentane sulfonic acid).

EXAMPLE 2

Equimolar amounts of 4-picoline and methyl iodide were combined with methanol and refluxed in a reaction vessel to produce a solution of N-methylpicolinium iodide. To the resulting solution was added one equivalent of 4-dimethylamino benzaldehyde and 100 mL of piperidine to produce a mixture. Said mixture was refluxed for 3 hours and then cooled to about 5°-10° C. Subsequent to filtration, 4-dimethylamino N-methylstilbazolium iodide was recovered (greater than 90% yield).

EXAMPLE 3

120 milligrams (1.2 mmole) cyclopentane sulfonic acid (as prepared in Example 1) and 213 milligrams (1.0 mmole) of silver(I) oxide were combined with 30 mL of acetonitrile solvent in a flask and stirred for 1 hour in the dark to produce a reaction mixture. The reaction mixture was filtered through a Celite pad and the solvent was removed. 310 milligrams (0.85 mmole) of 3-dimethylamino N-methylstilbazolium iodide (as prepared in Example 2) and 20 ml of methanol were added to the flask to produce a second mixture which was stirred overnight at room temperature. The second mixture was filtered through a Celite pad to remove the methanol solvent and a red solid precipitate. Said solid was dried in vacuo to yield 230 milligrams of 4'-dimethylamino N-methylstilbazolium cyclopentylsulfonate (90% yield).

The data in the table below has been compiled to confirm the high melting point of the compounds of the instant invention.

| Entry 1 | Stilbazolium Salt | Melting Point (°C.) |
| --- | --- | --- |
| 1 | DASMS | <219 |
| 2 | DAST | 259 |
| 3 | DASCp | 256 |

What is claimed is:

1. A stilbazolium salt having the formula

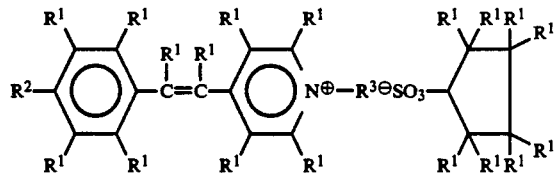

wherein each $R^1$ is independently hydrogen or deuterium, $R^2$ is HO—, $H_3CO$— or $(R^3)_2N$— and each $R^3$ is independently an aliphatic, alicyclic or aromatic radical.

2. A stilbazolium salt in accordance with claim 1, wherein each $R^3$ is independently
  (i) —$CH_3$,
  (ii) —$CDH_2$,
  (iii) —$CD_2H$ or
  (iv) $CD_3$.

3. A stilbazolium salt in accordance with claim 1, wherein said salt is 4'-dimethylamino-N-methylstilbazolium cyclopentanesulfonate and has the formula

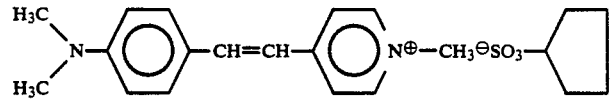

* * * * *